(12) United States Patent
Uhr et al.

(10) Patent No.: US 8,231,721 B2
(45) Date of Patent: Jul. 31, 2012

(54) ANTIFUNGAL LIQUID FORMULATIONS

(75) Inventors: Hermann Uhr, Leverkusen (DE); Tanja Gerharz, Duesseldorf (DE); Frank Sauer, Langenfeld (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 13/057,021

(22) PCT Filed: Jul. 28, 2009

(86) PCT No.: PCT/EP2009/059760
§ 371 (c)(1),
(2), (4) Date: Feb. 1, 2011

(87) PCT Pub. No.: WO2010/015552
PCT Pub. Date: Feb. 11, 2010

(65) Prior Publication Data
US 2011/0139033 A1    Jun. 16, 2011

(30) Foreign Application Priority Data
Aug. 5, 2008   (EP) ..................... 08161821

(51) Int. Cl.
*A01N 47/12* (2006.01)
*A01N 25/02* (2006.01)
*A01N 43/80* (2006.01)
*A01P 3/00* (2006.01)

(52) U.S. Cl. ............... 106/18.33; 106/15.05; 514/360

(58) Field of Classification Search ............... 106/15.05, 106/18.33; 514/360
See application file for complete search history.

(56) References Cited

U.S. PATENT DOCUMENTS

| | | | |
|---|---|---|---|
| 4,964,892 A | 10/1990 | Hsu | |
| 5,041,457 A | 8/1991 | Hsu | |
| 5,131,939 A | 7/1992 | Hsu | |
| 6,616,740 B2 | 9/2003 | Winkowski et al. | |
| 6,846,777 B2 | 1/2005 | Antoni-Zimmermann et al. | |
| 2004/0171600 A1* | 9/2004 | Ohnishi et al. | 514/184 |
| 2004/0198713 A1* | 10/2004 | Heer et al. | 514/184 |
| 2009/0293762 A1 | 12/2009 | Donders et al. | |
| 2010/0016390 A1 | 1/2010 | Lenoir et al. | |
| 2010/0286217 A1* | 11/2010 | Annis et al. | 514/372 |

FOREIGN PATENT DOCUMENTS

| | | |
|---|---|---|
| CA | 2053807 A1 | 4/1993 |
| EP | 1767091 A2 | 3/2007 |
| JP | 06016506 A | 1/1994 |
| JP | 07133205 A | 5/1995 |
| JP | 2003104801 A | 4/2003 |
| WO | WO2008/014820 A1 * | 2/2008 |

OTHER PUBLICATIONS

Search report issued in corresponding WO application No. PCT/EP2009/059760, consisting of 7 pages, [Feb. 2010 ].

* cited by examiner

*Primary Examiner* — Anthony J Green
(74) *Attorney, Agent, or Firm* — Nicanor A. Kohncke

(57) ABSTRACT

The invention relates to stable antifungal liquid formulations for protecting material, containing 3-iodopropynyl butyl carbamate (IPBC) and n-octylisothiazolinone (n-OIT).

5 Claims, No Drawings

ANTIFUNGAL LIQUID FORMULATIONS

The present invention relates to stable, antifungal liquid formulations for the protection of materials, comprising 3-iodopropargyl butylcarbamate (IPBC) and n-octylisothiazolinone (NOIT).

Formulations comprising IPBC and NOIT are known in principle. Thus, for example, CA 2053807 discloses synergistic mixtures of IPBC and NOIT for controlling the growth of *Klebsiella pneumoniae*, especially in open cooling systems and also in papermaking.

JP 06016506 discloses xylene- and water-containing compositions comprising IPBC and NOIT which are suitable for protecting wood, paper, textiles, adhesives and dyes against infestation by mold.

JP 2003104801 describes stable compositions comprising haloacetylene derivatives, isothiazolinones and epoxy compounds.

WO 2002/015693 discloses synergistic mixtures of pyrithione salts and 2-alkylisothiazolinones which can furthermore also comprise IPBC.

A disadvantage of the aforementioned mixtures and compositions is that they are either not VOC-free and/or have inadequate storage stability.

WO 03/049543 describes VOC-free or -reduced stable liquid formulations which comprise the active ingredient IPBC dissolved in polyethylene glycol, polypropylene glycol or polypropylene glycol glycerol ester.

Essentially VOC-free formulations comprising NOIT and IPBC are usually difficult to stabilize since IPBC is decomposed in the presence of heat or light. As a consequence of this, such formulations become discolored and are thus no longer suitable for many applications.

One option of obtaining VOC-free formulations consists in formulating the active ingredients as aqueous dispersions without additional solvents. While IPBC and NOIT can in each case be formulated in stable dispersions or emulsions by themselves, it is not possible to obtain stable dispersions which comprise both active ingredients. The presence of both active ingredients leads to severe heteroflocculation, which leads to the formation of agglomerates after a short time and to severe sedimentation of the formulation and/or oiling-out of NOIT.

Essentially VOC-free, stable liquid formulations of NOIT and IPBC are not known to date.

There was therefore a need to provide essentially VOC-free, stable liquid formulations of NOIT and IPBC.

Liquid compositions have now been found, comprising at least
3-iodopropargyl butylcarbamate (IPBC)
n-octylisothiazolinone (NOIT)
a solvent which, based on standard pressure (1013.25 hPa), has a boiling point of 250° C. or more and comprises at least two functional groups which are selected from ether, ester or amide or alcohol groups,
where the liquid compositions are essentially free from solvents which, based on standard pressure, have a boiling point of less than 250° C.

It may be noted at this point that the scope of the invention encompasses all arbitrary and possible combinations of the components, value ranges and/or process parameters above and below given generally or in preferred ranges.

Within the scope of the invention, the term "liquid composition" means that the composition is present at room temperature in the liquid state and the content of solid constituents is 0 to 1% by weight, preferably 0 to 0.5% by weight. The liquid compositions are particularly preferably free from solid constituents.

Essentially free from solvents which, based on standard pressure, have a boiling point of less than 250° C. means a weight fraction of such solvents in the formulation of from to 3% by weight, preferably 0 to 1% by weight and particularly preferably 0 to 0.5% by weight.

By way of example, the liquid compositions according to the invention comprise IPBC and NOIT in a weight ratio of from 90:1 to 1:90, preferably 8:2 to 2:8 and very particularly preferably 7:3 to 3:7.

The sum of the active ingredient contents of IPBC and NOIT in the liquid compositions according to the invention can be varied in a wide range and is limited upwards only by the maximum solubility of the active ingredients in the selected solvent. In general, for example 2 to 90% by weight of IPBC and NOIT, based on the sum of their weight fractions, may be present in the formulation, preferably 5 to 85% by weight, very particularly preferably 30 to 80% by weight and even further preferably 50 to 60% by weight.

The liquid compositions according to the invention furthermore comprise at least one solvent which, based on standard pressure (1013.25 hPa), has a boiling point of 250° C. or more and contains at least two functional groups which are selected from ether, ester or amide or alcohol groups.

Such solvents are preferably polyether alcohols, such as, for example, polyethylene glycols and polypropylene glycols, and also dialkyl diesters such as dialkyl adipates, dialkyl succinates and dialkyl glutarates.

Particularly preferred solvents are polyethylene glycols and also dialkyl adipates, dialkyl succinates and dialkyl glutarates, and mixtures of the aforementioned solvents.

Polyethylene glycols are preferably those which have at least three ethylene glycol units. Preferred polyethylene glycols have 3 to 14, preferably 3 to 12 and particularly preferably 3 to 10, polyethylene glycol units. Very particular preference is given to triethylene glycol, tetraethylene glycol, polyethylene glycol 200, polyethylene glycol 300, polyethylene glycol 400, polyethylene glycol 500 and polyethylene glycol 600. These may be the pure compounds or mixtures thereof. The specified polyethylene glycols and their mixtures are commercially available.

Dialkyl glutarates, succinates and adipates can be used for example individually, but preferably as a mixture, as are produced in the industrial production process. Preference is given to using those esters in which the alkyl radical is straight-chain or branched and has between 3 and 10 carbon atoms. They are particularly preferably the propyl, n-butyl, isobutyl, s-butyl, n-pentyl, n-hexyl, n-heptyl, n-octyl, 2-ethylheyl diesters or mixtures thereof, very particularly preferably mixtures of the diisobutyl diesters.

The amount of such solvents can vary within a wide range. In general, 5 to 90% by weight, preferably 5 to 48% by weight and very particularly preferably 40 to 48% by weight, of solvents are used in the formulations.

The compositions according to the invention can furthermore optionally comprise at least one emulsifier. Suitable emulsifiers are, for example, nonionic and anionic emulsifiers.

By way of example, the following suitable emulsifiers may be mentioned: polyoxyethylene or polyoxypropylene fatty acid esters, polyoxyethylene or polyoxypropylene fatty alcohol ethers, alkylphenyl ethoxylates or propoxylates, trisarylphenyl ethoxylates or propoxylates, polyvinylpyrrolidones, polyacrylates, alkyl polyglycosides, fatty amine ethoxylates, fatty acid amide ethoxylates, alkylpolyalkylene glycol copolymers, block copolymers of polyoxypropylene and polyoxyethylene units which have been optionally etherified with alcohols, alkylphenyl groups or trisarylphenyl radicals or have been esterified with fatty acids, or surfactants of the aforementioned types which additionally also carry sulfonate or phosphate radicals, and also furthermore alkylsulfonates, alkyl sulfates, arylsulfonates.

The emulsifiers are preferably nonionogenic emulsifiers such as polyoxyethylene fatty acid esters, polyoxyethylene fatty alcohol ethers, alkylphenyl ethoxylates, trisarylphenyl ethoxylates, polyvinylpyrrolidones, polyacrylates, block copolymers of polyoxypropylene and polyoxyethylene units which have optionally been etherified with alcohols, alkylphenyl groups or trisarylphenyl radicals or have been esterified with fatty acids, or mixtures of the aforementioned emulsifiers.

The liquid compositions according to the invention preferably comprise 0.001 to 10% by weight, preferably 1 to 8% by weight and very particularly preferably to 1 to 6% by weight of emulsifiers.

The liquid compositions according to the invention can optionally also comprise further active ingredients such as, for example, fungicides, bactericides, algicides and/or insecticides.

Fungicides, bactericides, algicides and/or insecticides which are optionally additionally present that can be used are, for example:

triazoles such as azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazole, penconazole, propioconazole, prothioconazole, simeoconazole, (±)-cis-1-(4-chlorophenyl)-2-(1H-1,2,4-triazol-1-yl) cycloheptanol, 2-(1-tert-butyl)-1-(2-chlorophenyl)-3-(1,2,4-triazol-1-yl)propan-2-ol, tebuconazole, tetraconazole, triadimefon, triadimenol, triapenthenol, triflumizole, triticonazole, uniconazole, and their metal salts and acid adducts;

imidazoles such as clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chlorophenoxy)-3,3-dimethylbutan-2-one, and their metal salts and acid adducts;

pyridines and pyrimidines such as ancymidol, buthiobate, fenarimol, mepanipyrin, nuarimol, pyroxyfur, triamirol;

succinate dehydrogenase inhibitors such as benodanil, carboxim, carboxim sulfoxide, cyclafluramid, fenfuram, flutanil, furcarbanil, furmecyclox, mebenil, mepronil, methfuroxam, metsulfovax, nicobifen, pyrocarbolid, oxycarboxin, shirlan, seedvax;

naphthalene derivatives such as terbinafin, naftifin, butenafin, 3-chloro-7-(2-aza-2,7,7-trimethyl-oct-3-ene-5-yne);

sulfenamides such as dichlofluanid, tolylfluanid, folpet, fluorfolpet; captan, captofol;

benzimidazoles such as carbendazim, benomyl, fuberidazole, thiabendazole or their salts;

morpholine derivatives such as aldimorph, dimethomorph, dodemorph, falimorph, fenpropidin, fenpropimorph, tridemorph, trimorphamid and their arylsulfonate salts, such as e.g. p-toluenesulfonic acid and p-dodecyl-phenylsulfonic acid;

benzothiazoles such as: 2-mercaptobenzothiazole;

benzothiophene dioxides such as: cyclohexyl-benzo[b] thiophenecarboxamide S,S-dioxide;

benzamides such as: 2,6-dichloro-N-(4-trifluoro-methyl-benzyl)benzamide, tecloftalam;

boron compounds such as: boric acid, boric acid esters, borax;

formaldehyde and formaldehyde-releasing compounds such as benzyl alcohol mono(poly)hemiformal, 1,3-bis(hydroxymethyl)-5,5-dimethylimidazolidine-2,4-dione (DM-DMH), bisoxazolidine, n-butanol hemiformal, cis-1-(3-chloroallyl)-3,5,7-triaza-1-azoniaadamantane chloride, 1-[1,3-bis(hydroxymethyl-2,5-dioxoimidazolidin-4-yl]-1,3-bis (hydroxymethyl)urea, dazomet, dimethylolurea, 4,4-dimethyloxazolidine, ethylene glycol hemiformal, 7-ethylbicyclooxazolidine, hexahydro-5-triazine, hexamethylenetetramine, N-hydroxymethyl-N'-methylthiourea, methylenebismorpholine, sodium N-(hydroxymethyl)glycinate, N-methylolchloroacetamide, oxazolidine, paraformaldehyde, taurolin, tetrahydro-1,3-oxazine, N-(2-hydroxypropyl)-aminomethanol, tetramethylolacetylenediurea (TMAD);

isothiazolinones such as: N-methylisothiazolin-3-one, 5-chloro-N-methylisothiazolin-3-one, 4,5-trimethylene-isothiazolinone, 4,5-benzoisothiazolinone;

aldehydes such as: cinnamaldehyde, formaldehyde, glutardialdehyde, β-bromocinnamaldehyde, o-phthaldialdehyde;

thiocyanates such as: thiocyanatomethylthiobenzothiazole, methylenebisthiocyanate;

quaternary ammonium compounds and guanidines such as: benzalkonium chloride, benzyldimethyltetradecylammonium chloride, benzyldimethyldodecylammonium chloride, dichlorobenzyldimethylalkylammonium chloride, didecyldimethylammonium chloride, dioctyldimethylammonium chloride, N-hexadecyltrimethylammonium chloride, 1-hexadecylpyridinium chloride, iminoctadine tris(albesilate);

iodine derivatives such as: diiodomethyl p-tolyl sulfone, 3-iodo-2-propynyl alcohol, 4-chlorophenyl-3-iodo-propargylformal, 3-bromo-2,3-diiodo-2-propenyl ethylcarbamate, 2,3,3-triiodoallyl alcohol, 3-bromo-2,3-diiodo-2-propenyl alcohol, 3-iodo-2-propynyl n-hexylcarbamate, 3-iodo-2-propynyl cyclohexylcarbamate, 3-iodo-2-propynyl phenylcarbamate;

phenols such as: tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, methyl p-hydroxybenzoate, ethyl p-hydroxybenzoate, propyl p-hydroxybenzoate, butyl p-hydroxybenzoate, octyl p-hydroxybenzoate, o-phenylphenol, m-phenylphenol, p-phenylphenol, 4-(2-tert-butyl-4-methylphenoxy)phenol, 4-(2-isopropyl-4-methylphenoxy) phenol, 4-(2,4-dimethylphenoxy)phenol and their alkali metal salts and alkaline earth metal salts;

microbicides with an activated halogen group such as: bronidox, 2-bromo-2-nitro-1,3-propanediol, 2-bromo-4'-hydroxyacetophenone, 1-bromo-3-chloro-4,4,5,5-tetramethyl-2-imidazolidinone, β-bromo-β-nitrostyrene, chloroacetamide, chloramine T, 1,3-dibromo-4,4,5,5-tetramethyl-2-imidazolidinone, dichloramine T, 3,4-dichloro-(3H)-1,2-dithiol-3-one, 2,2-dibromo-3-nitrile-propionamide, 1,2-dibromo-2,4-dicyanobutane, halane, halazone, mucochloric acid, phenyl (2-chlorocyanovinyl) sulfone, phenyl (1,2-dichloro-2-cyanovinyl) sulfone, trichloroisocyanuric acid;

pyridines such as: 1-hydroxy-2-pyridinethione (and their Cu, Na, Fe, Mn, Zn salts), tetrachloro-4-methyl-sulfonylpyridine, pyrimethanol, mepanipyrim, dipyrithione, 1-hydroxy-4-methyl-6-(2,4,4-trimethylpentyl)-2-(1H)-pyridine;

methoxyacrylates or similar such as: azoxystrobin, dimoxystrobin, fluoxastrobin, kresoxim-methyl, metominostrobin, orysastrobin, picoxystrobin, pyraclostrobin, trifloxystrobin, 2,4-dihydro-5-methoxy-2-methyl-4-[2-[[[[1-[3-(trifluoromethyl)phenyl]ethylidene]-amino]oxy]methyl]phenyl]-3H-1,2,4-triazol-3-one (CAS No. 185336-79-2);

metal soaps such as: salts of the metals tin, copper and zinc with higher fatty acids, resin acids, naphthenoic acids and phosphoric acid, such as, for example, tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

metal salts such as salts of the metals tin, copper, zinc, and also chromates and dichromates, such as e.g. copper hydroxycarbonate, sodium dichromate, potassium dichromate, potassium chromate, copper sulfate, copper chloride, copper borate, zinc fluorosilicate, copper fluorosilicate;

oxides such as: oxides of the metals tin, copper and zinc, such as e.g. tributyltin oxide, $Cu_2O$, CuO, ZnO;

oxidizing agents such as hydrogen peroxide, peracetic acid, potassium persulfate;

dithiocarbamates such as cufraneb, ferban, potassium N-hydroxymethyl-N'-methyldithiocarbamate, sodium or potassium dimethyldithiocarbamate, mancozeb, maneb, metam, metiram, thiram, zineb, ziram;

nitriles such as 2,4,5,6-tetrachloroisophthalodinitrile, disodium cyanodithioimidocarbamate;

quinolines such as: 8-hydroxyquinoline and their Cu salts;

other fungicides and bactericides such as bethoxazin, 5-hydroxy-2(5H)-furanone; 4,5-benzodithiazolinone, 4,5-trimethylenedithiazolinone, N-(2-p-chlorobenzoyl-ethyl)hexaminium chloride, 2-oxo-2-(4-hydroxyphenyl)-acetchydroximoyl chloride, tris-N-(cyclohexyldiazeniumdioxy)aluminum, N-(cyclohexyldiazeniumdioxy)-tributyltin or K salts, bis-N-(cyclohexyldiazeniumdioxy)copper; iprovalicarb, fenhexamide, spiroxamine, carpropamid, diflumetorin, quinoxyfen, famoxadone, polyoxorim, acibenzolar S-methyl, furametpyr, thifluzamide, methalaxyl-M, benthiavalicarb, metrafenon, cyflufenamid, tiadinil, tea tree oil, phenoxyethanol, Ag, Zn or Cu-containing zeolites alone or enclosed in polymeric materials.

The fungicides and bactericides are very particularly preferably:

azaconazole, bromuconazole, cyproconazole, dichlobutrazol, diniconazole, hexaconazole, metaconazole, penconazole, propiconazole, tebuconazole, dichlofluanid, tolylfluanid, triadimefon, fluorfolpet, methfuroxam, carboxin, cyclohexyl-benzo[b]thiophenecarboxamide S,S-dioxide, fenpiclonil, 4-(2,2-difluoro-1,3-benzodioxol-4-yl)-1H-pyrrole-3-carbonitrile, butenafine, imazalil, N-methylisothiazolin-3-one, 5-chloro-N-methylisothiazolin-3-one, dichloro-N-octylisothiazolinone, mercaptobenzothiazole, thiocyanatomethylthiobenzothiazole, thiabendazole, benzoisothiazolinone, N-(2-hydroxypropyl)aminomethanol, benzyl alcohol (hemi)formal, N-methylolchloroacetamide, N-(2-hydroxypropyl)aminemethanol, glutaraldehyde, omadine, Zn omadine, dimethyl dicarbonate, 2-bromo-2-nitro-1,3-propanediol, bethoxazin, o-phthaldialdehyde, 2,2-dibromo-3-nitrilepropionamide, 1,2-dibromo-2,4-dicyanobutane, 1,3-bis(hydroxymethyl)-5,5-dimethylimidazolidine-2,4-dione (DMDMH), tetramethylolacetylenediurea (TMAD), ethylene glycol hemiformal, p-hydroxybenzoic acid, carbendazim, chlorophene, 3-methyl-4-chlorophenol, o-phenylphenol.

The algicides are preferably:

acetochlor, acifluorfen, aclonifen, acrolein, alachlor, alloxydim, ametryn, amidosulfuron, amitrole, ammonium sulfamate, anilofos, asulam, atrazine, azafenidin, aziptrotryne, azimsulfuron, benazolin, benfluralin, benfuresate, bensulfuron, bensulfide, bentazone, benzofencap, benzthiazuron, bifenox, bispyribac, bispyribac-sodium, borax, bromacil, bromobutide, bromofenoxim, bromoxynil, butachlor, butamifos, butralin, butylate, bialaphos, benzoyl-prop, bromobutide, butroxydim, carbetamide, carfentrazone-ethyl, carfenstrole, chlomethoxyfen, chloramben, chlorbromuron, chlorflurenol, chloridazon, chlorimuron, chlornitrofen, chloroacetic acid, chloransulam-methyl, cinidon-ethyl, chlorotoluron, chloroxuron, chlorpropham, chlorsulfuron, chlorthal, chlorthiamid, cinmethylin, cinosulfuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhalofop, cyhalofop-butyl, clopyrasuluron, cyclosulfamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn, eglinazine, endothal, EPTC, esprocarb, ethalfluralin, ethidimuron, ethofumesate, ethobenzanid, ethoxyfen, ethametsulfuron, ethoxysulfuron, fenoxaprop, fenoxaprop-P, fenuron, flamprop, flamprop-M, flazasulfuron, fluazifop, fluazifop-P, fuenachlor, fluchloralin, flufenacet, flumeturon, fluoroglycofen, fluoronitrofen, flupropanate, flurenol, fluridone, fluorochloridone, fluoroxypyr, fomesafen, fosamine, fosametine, flamprop-isopropyl, flamprop-isopropyl-L, flufenpyr, flumiclorac-pentyl, flumipropyn, flumioxzim, flurtamone, flumioxzim, flupyrsulfuron-methyl, fluthiacet-methyl, glyphosate, glufosinate-ammonium haloxyfop, hexazinone, imazamethabenz, isoproturon, isoxaben, isoxapyrifop, imazapyr, imazaquin, imazethapyr, ioxynil, isopropalin, imazosulfuron, imazomox, isoxaflutole, imazapic, ketospiradox, lactofen, lenacil, linuron, MCPA, MCPA-hydrazide, MCPA-thioethyl, MCPB, mecoprop, mecoprop-P, mefenacet, mefluidide, mesosulfuron, metam, metamifop, metamitron, metazachlor, methabenzthiazuron, methazole, methoroptryne, methyldymron, methyl isothiocyanate, metobromuron, metoxuron, metribuzin, metsulfuron, molinate, monalide, monolinuron, MSMA, metolachlor, metosulam, metobenzuron, naproanilide, napropamide, naptalam, neburon, nicosulfuron, norflurazon, sodium chlorate, oxadiazon, oxyfluorfen, oxysulfuron, orbencarb, oryzalin, oxadiargyl, propyzamide, prosulfocarb, pyrazolate, pyrazosulfuron, pyrazoxyfen, pyribenzoxim, pyributicarb, pyridate, paraquat, pebulate, pendimethalin, pentachlorophenol, pentoxazone, pentanochlor, petroleum oils, phenmedipham, picloram, piperophos, pretilachlor, primisulfuron, prodiamine, profoxydim, prometryn, propachlor, propanil, propaquizafob, propazine, propham, propisochlor, pyriminobac-methyl, pelargonic acid, pyrithiobac, pyraflufen-ethyl, quinmerac, quinocloamine, quizalofop, quizalofop-P, quinchlorac, rimsulfuron sethoxydim, sifuron, simazine, simetryn, sulfosulfuron, sulfometuron, sulfentrazone, sulcotrione, sulfosate, tar oils, TCA, TCA-sodium, tebutam, tebuthiuron, terbacil, terbumeton, terbuthylazine, terbutryn, thiazafluoron, thifensulfuron, thiobencarb, thiocarbazil, tralkoxydim, triallate, triasulfuron, tribenuron, triclopyr, tridiphane, trietazine, trifluralin, tycor, thdiazimin, thiazopyr, triflusulfuron, vernolate.

The algicides are very particularly preferably triazine compounds, such as, for example, terbutryn, cybutryn, propazine or terbutone, urea compounds, such as, for example, diuron, benzthiazuron, methabenzthiazuron, tebuthiuron, and isoproturon, or uracils such as, for example, terbacil.

The liquid compositions according to the invention can optionally additionally comprise stabilizers from the class of oxidation inhibitors, free-radical scavengers and UV absorbers, or not in each case independently of one another.

In one preferred embodiment, the liquid compositions according to the invention comprise no further fungicides, bactericides, algicides and/or insecticides.

In a further preferred embodiment, the liquid compositions according to the invention comprise no epoxides.

In a further preferred embodiment, the liquid compositions according to the invention comprise no stabilizers from the group of formic acid, formate salts or formate esters.

In a particularly preferred embodiment, the liquid compositions according to the invention comprise 20 to 35% by weight of IPBC, 10 to 25% by weight of NOIT, 40 to 48% by weight of solvent and 1 to 6% by weight of emulsifiers, where the sum of the four aforementioned components is 90 to 100%, preferably 95 to 100% and particularly preferably to 100%, by weight, based on the total mass of the liquid compositions.

In a yet further preferred embodiment, the aforementioned liquid compositions include no further active ingredients, no epoxides and no stabilizers from the group of formic acid, formate salts or formate esters.

The liquid compositions according to the invention can be prepared for example in a manner known per se by mixing the individual components.

The invention further relates to the use of the liquid compositions according to the invention for protecting industrial materials. Suitable industrial materials are in particular adhesives, glues, paper, card, leather, wood, woodbase materials, wood/plastic composites, paints, coating compositions, plasters, cooling lubricants and heat transfer liquids. Very particular preference is given to paints, coating compositions, plasters, wood and woodbase materials.

The invention moreover relates to a method of protecting industrial materials against infestation and/or decomposition by microorganisms, which is characterized in that the liquid compositions according to the invention are left to act in undiluted form or diluted form on the microorganism or its habitat.

The invention moreover relates to industrial materials obtainable by treating industrial materials with the liquid compositions according to the invention.

In the case of paints and coating compositions, both the still liquid, and also the dried system are protected against infestation by microorganisms, particularly fungi and algae.

Examples of microorganisms which can bring about degradation or alteration of the industrial materials include bacteria, fungi, yeasts, algae and slime organisms. The liquid compositions according to the invention are preferably used to combat fungi, in particular molds, wood-discoloring and wood-destroying fungi (Basidiomycetes) and also to combat algae.

Mention may be made for example of microorganisms of the following genera:

*Alternaria*, such as *Alternaria tenuis*, *Aspergillus*, such as *Aspergillus niger*, *Chaetomium*, such as *Chaetomium globosum*, *Coniophora*, such as *Coniophora puetana*, *Lentinus*, such as *Lentinus tigrinus*, *Penicillium*, such as *Penicillium glaucum*, *Polyporus*, such as *Polyporus versicolor*, *Aureobasidium*, such as *Aureobasidium pullulans*, *Sclerophoma*, such as *Sclerophoma pityophila*, *Trichoderma*, such as *Trichoderma viride*, *Escherichia*, such as *Escherichia coli*, *Pseudomonas*, such as *Pseudomonas aeruginosa* and *Staphylococcus*, such as *Staphylococcus aureus*.

The application rate of the liquid compositions according to the invention is governed by the type and incidence of the microorganisms to be controlled and also by the composition of the material to be protected. The optimum use amount can be determined easily and in a manner sufficiently known to the person skilled in the art by means of test series. In general, 0.001 to 5% by weight of the liquid composition according to the invention, preferably from 0.01 to 1.0% by weight, based on the material to be protected, are used.

The particular advantage of the liquid compositions according to the invention is that they are very readily storage-stable even at elevated temperatures and do not crystallize out even at temperatures below 0° C. Furthermore, it has been found that the formulations only become slightly discolored upon storage and can also be incorporated into the industrial material to be protected in the simplest of manners. Furthermore, the compositions according to the invention permit the formulation of unexpectedly high active ingredient concentrations of IPBC and NOIT.

EXAMPLES

Example 1

A solution consisting of 6.7 g of Rhodiasolv DIB (a mixture of the isobutyl diesters of glutaric acid, succinic acid and adipic acid), 15.22 g of polyethylene glycol 300 and 2.50 g of Antarox B 500 (butylpolyoxypropylene-polyoxyethylene block copolymer, CAS No. 9038-95-3) was admixed with IPBC and NOIT (weight ratio 5:3) at room temperature until nothing more dissolved. The resulting solution comprised 34.51 g of NOIT (29.5% based on total solution) and 57.95 g (49.9% based on total solution) of IPBC. Over the course of a week at room temperature, no precipitations were observed.

Example 2

A solution consisting of 15.22 g of polyethylene glycol 300 and 2.50 g of Antarox B 500 was admixed with IPBC and NOIT (weight ratio 5:3) at room temperature until nothing more dissolved. The resulting solution comprised 25.9 g of NOIT (29.7% based on total solution) and 43.6 g (50.0% based on total solution.) of IPBC. Over the course of a week at room temperature, no precipitations were observed.

Example 3

15.22 g of polyethylene glycol 300 are introduced as initial charge and admixed with IPBC and NOIT (ratio 5:3) at room temperature until nothing more dissolved. The resulting solution comprised 25.8 g of NOIT (29.7% based on total solution) and 43.6 g (51.5% based on total solution) of IPBC. Over the course of a week at room temperature, no precipitations were observed.

Examples 4 to 6

The solutions stated in the table were prepared by mixing, stored for 2 weeks at 54° C. and then assessed analytically and visually.

| -/Example No. | 4 | 5 | 6 |
|---|---|---|---|
| IPBC | 32.16 | 32.16 | 32.16 |
| NOIT | 19.09 | 19.09 | 19.09 |
| Rhodiasolv DIB[1)] | 13.40 | — | 13.40 |
| Polyethylene glycol 300 | 30.43 | 43.83 | 30.43 |
| Antarox B 500 | 5.0 | 5.0 | 5.0 |
| Content of IPBC (after 2 weeks at 55° C.) | 32.0 | 30.5 | 32.0 |
| Content of NOIT (after 2 weeks at 55° C.) | 19.1 | 18.9 | 19.1 |
| Appearance (after 2 weeks at 54° C.) | clear, pale yellow solution | clear, pale yellow solution | clear, pale yellow solution |
| Appearance (after one week at −4° C.) | clear, colorless solution | clear, colorless solution | clear, colorless solution |

All data for the components in % by weight

Example 7

For Comparison

Solubility of IPBC in Rhodiasolv DIB and PEG 300

The solvent was introduced as initial charge at room temperature, and IPBC was added until a sediment persisted. It was after-stirred for a further 12 h, the solid was centrifuged off and the remaining supernatant was analyzed by means of HPLC. Here, a solubility of IPBC in Rhodiasolv DIB of 36.1% by weight and in polyethylene glycol 300 of 44.9% by weight was ascertained.

What is claimed is:

1. A liquid composition, comprising:
   3-iodopropargyl butylcarbamate (IPBC)
   n-octylisothiazolinone (NOIT)
   a solvent having a boiling point of 250° C. or more, based on standard pressure, and which comprises at least two functional groups selected from the group consisting of ether, ester, amide, and alcohol groups, and
   wherein the liquid composition is essentially free from further solvents having a boiling point of less than 250° C., based on standard pressure, and
   further wherein said 3-iodopropargyl butylcarbamate (IPBC) is present in an amount of 20 to 35% by weight, said n-octylisothiazolinone (NOIT) is present in an amount of 10 to 25% by weight, and the solvent is present in an amount of 40 to 48% by weight, and further comprising an emulsifier present in an amount of 1 to 6% by weight, and wherein the sum of the four aforementioned components is 90 to 100% by weight, based on the total mass of the liquid composition.

2. A process for protecting an industrial material, comprising:
   treating the industrial material with the liquid composition according to claim 1.

3. The process according to claim 2 wherein the industrial material is selected from the group consisting of adhesives, glues, paper, card, leather, wood, woodbase materials, wood/plastic composites, paints, coating compositions, plasters, cooling lubricants and heat transfer liquids.

4. A treated industrial material obtained by treating an industrial material with the liquid composition according to claim 1, thereby forming said treated industrial material.

5. A method of protecting an industrial material against infestation and/or decomposition by microorganisms, comprising:
   contacting the microorganism or its habitat with the liquid composition according to claim 1, wherein said composition may be in a diluted or an undiluted form.

* * * * *